United States Patent
Goss (10) Patent No.: US 12,285,358 B2
(45) Date of Patent: Apr. 29, 2025

(54) LENS APPLICATOR

(71) Applicant: Sixth Sense IP Pty Ltd, South Melbourne (AU)

(72) Inventor: Anthony Goss, South Melbourne (AU)

(73) Assignee: Sixth Sense IP Pty Ltd, South Melbourne (AU)

( * ) Notice: Subject to any disclaimer, the term of this patent is extended or adjusted under 35 U.S.C. 154(b) by 761 days.

(21) Appl. No.: 17/605,632

(22) PCT Filed: Apr. 22, 2020

(86) PCT No.: PCT/AU2020/050392
§ 371 (c)(1),
(2) Date: Oct. 22, 2021

(87) PCT Pub. No.: WO2020/215121
PCT Pub. Date: Oct. 29, 2020

(65) Prior Publication Data
US 2022/0218523 A1 Jul. 14, 2022

(30) Foreign Application Priority Data
Apr. 22, 2019 (AU) .................... 2019901379

(51) Int. Cl.
*B25J 13/08* (2006.01)
*A61F 9/00* (2006.01)
(Continued)

(52) U.S. Cl.
CPC ........... *A61F 9/0061* (2013.01); *B25J 11/008* (2013.01); *B25J 13/08* (2013.01); *B25J 15/0028* (2013.01);
(Continued)

(58) Field of Classification Search
CPC ....... A61F 9/0061; B25J 11/008; B25J 13/08; B25J 13/086; B25J 15/0616
(Continued)

(56) References Cited

U.S. PATENT DOCUMENTS 4,123,098 A * 10/1978 Shoup .................. A61F 9/0061
294/187
4,378,126 A 3/1983 Procenko
(Continued)

FOREIGN PATENT DOCUMENTS

CN 102481735 A 5/2012
CN 109044608 A 12/2018
(Continued)

OTHER PUBLICATIONS

International Search Report and Written Opinion for Application No. PCT/AU2020/050392 dated Aug. 10, 2020 (10 pages).
(Continued)

*Primary Examiner* — Douglas A Hess
(74) *Attorney, Agent, or Firm* — Michael Best & Friedrich LLP (57) ABSTRACT

A contact lens applicator is described which automatically applies a contact lens to a user's, or a patients, eye. Embodiments described include a contact lens applicator which includes: a main tool base for housing control system elements; a robotic arm mounted on the tool base; an end effector mounted on an end of the robotic arm for grasping a contact lens for delivery to an eye of the user.

19 Claims, 10 Drawing Sheets (51) Int. Cl.
  *B25J 11/00* (2006.01)
  *B25J 15/00* (2006.01)
  *B25J 15/06* (2006.01)
(52) U.S. Cl.
  CPC ....... *B25J 15/0066* (2013.01); *B25J 15/0616* (2013.01)
(58) Field of Classification Search
  USPC .......................................................... 294/1.2
  See application file for complete search history.

(56) References Cited

U.S. PATENT DOCUMENTS

| | | | |
|---|---|---|---|
| 5,913,556 A | 6/1999 | Perusse | |
| 6,739,636 B2 * | 5/2004 | Py | A61F 9/0061 294/1.2 |
| 7,178,666 B2 * | 2/2007 | Huang | A45C 11/005 206/804 |
| 10,195,746 B2 | 2/2019 | Truebenbach | |
| 10,238,285 B2 * | 3/2019 | Farley | A61F 9/00736 |
| 2005/0263412 A1 | 12/2005 | Huang | |
| 2006/0017297 A1 | 1/2006 | Py | |
| 2006/0131904 A1 | 6/2006 | Mears | |
| 2011/0284396 A1 | 11/2011 | Pugh et al. | |
| 2016/0089793 A1 | 3/2016 | Truebenbach | |

FOREIGN PATENT DOCUMENTS

| | | | |
|---|---|---|---|
| CN | 109129485 A | | 1/2019 |
| CN | 208468379 U | | 2/2019 |
| CN | 109419555 A | | 3/2019 |
| FR | 2748930 A1 | | 11/1997 |
| KR | 20090077445 A | * | 7/2009 |
| WO | 2014060264 A1 | | 4/2014 |
| WO | 2018044861 A1 | | 3/2018 |

OTHER PUBLICATIONS

Chinese Patent Office Action for Application No. 202080045845.6 dated Jul. 29, 2023 (28 pages including English machine translation).
European Supplementary Search Report and Written Opinion for U.S. Appl. No. 20/794,085 dated Dec. 15, 2022 (4 pages).

* cited by examiner

LENS APPLICATOR

TECHNICAL FIELD

The present technology relates generally to a tool for applying a contact lens to an eye of a user or a patient. The tool is particularly suited to self-application but it is also very useful for application to a patient, that is, a person other than the user.

BACKGROUND

A common experience among people with myopia or hyperopia is that they want to use contact lenses to access the benefit of freedom from eyeglass frames, but they find it terrifying to apply them to their eyes. To give an idea about the prevalence of this experience, an internet search for "fear of contact lenses" yields 12 500 000 results in 0.48 seconds when using one particular search engine.

There are known contact lens applicators but none appear to have much flexibility. U.S. Pat. No. 4,378,126 to Procenko has a hollow lens extension tube and a light directed therealong. The light allows a user to aim the lens at the eye and then apply the lens to their eye. This mechanism still has a drawback, in that it requires a person to drive the lens toward their own eye, which is an action which causes many users to panic.

People who use contact lenses do so because they have poor vision. So, when self-administering contact lenses, they do so without their eyeglasses, which, to see clearly, they need. Everything the person sees is blurred, making it difficult to apply the contact lens to their eye. There are many kinds of disease which can make it more difficult to apply the contact lens to the eye, including MS, Parkinsons, stroke, tremors, both essential and dystonic, alcohol withdrawal, and others.

Since contact lenses are worn directly on the cornea of the eye, it is useful for them to be handled with exceptional care to prevent eye infections, ulcerations and other eye diseases. Careless handling or storage of contact lenses, or sleeping with the lenses on can have severe implications after the lenses are worn and remains a key challenge hindering the large-scale take-up and usage of contact lenses, particularly among skeptical consumers.

It is estimated that 99 percent of contact lens wearers have engaged in at least one "contact lens hygiene risk behaviour" known to increase the chances of developing eye infection or inflammation. Also, it is estimated that about one-third of contact lens wearing people have had to visit a doctor because of eye redness or pain caused by their contact lenses.

In addition, medical practitioners in developing countries are not well equipped to prescribe contact lenses, which also threatens to limit the overall growth prospects of the global contact lens market.

Nevertheless, the market for contact lenses in the Asia Pacific region and elsewhere is expected to expand.

In 2015 it is estimated that there were 41 million contact users in the United States, which is about 30% of the global market, such that, in 2015, the global market was estimated at about 137 million users. Demand for contact lens is projected to grow at approximately 6% per annum. The contact user dropout rate varies between about 16%-31% (median 23.5%) of new users per annum. Of the total dropouts, approximately 27% have difficulty inserting & removing lens. Of the total dropouts, approximately 10-17% have eye infection issues.

Much current contact lens research is directed towards the treatment and prevention of conditions resulting from contact lens contamination and colonization by foreign organisms. Clinicians tend to agree that one complication of contact lens wear is microbial keratitis and that one of the microbial pathogens is *Pseudomonas aeruginosa*.

The present inventor seeks to provide a new contact lens applicator that seeks to ameliorate one or more of the above mentioned disadvantages.

SUMMARY

Broadly, the present technology provides a contact lens applicator which automatically applies or removes a contact lens to, or from, a user's, or a patient's, eye. Embodiments of the contact lens applicator do not require a person or operator to come into contact with the contact lens before it is placed in the eye, or during the removal operation, so the contact lens application or removal operation is carried out in a substantially sterile environment.

Advantageously the present technology facilitates self-application of a contact lens.

In accordance with one aspect of the present technology there is provided a contact lens applicator which includes:
  a main tool base for housing a control system;
  a robotic arm mounted on the tool base;
  an end effector mounted on an end of the robotic arm for grasping a contact lens for delivery to an eye of the user.

The arrangement is such that, in embodiments, the robotic arm is caused and/or configured to execute a programmed sequence of tasks including:
  grasping a contact lens payload;
  identifying target eye for contact lens; and
  delivery of contact lens to target eye.

Further programmed steps or routines for embodiments of the contact lens applicator include:
  cleaning end effector;
  opening contact lens magazine closure;
  returning robotic arm to standby position;
  detecting obstructions;
  retraction of robotic arm if obstruction is encountered;
  retraction of robotic arm to standby position when the contact lens is delivered to the target eye.

In accordance with another aspect of the present technology there is provided a method of delivering a contact lens to a target eye with a robotic arm mounted on a main tool base, the method including the steps of:
  extracting a contact lens from a contact lens reservoir with the robotic arm;
  receiving in a computer processor, data from one or more sensors regarding a target eye and/or face;
  delivering the contact lens to a target eye on the target eye and/or face using real-time data from the sensor;
  retracting the robotic arm to a stowed position.

Advantageously, in some embodiments the method includes the step of compensating for movements of a base on which the robotic arm is mounted, to facilitate self-administration of the contact lens while holding the contact lens in a user's own hand.

In one embodiment, the robotic arm includes one or more telescopic arms for extending the contact lens toward the target eye.

In one embodiment, the robotic arm is articulating, in that it includes a plurality of articulated arms.

In one embodiment, the robotic arm includes three articulating arms, connected together by hinged joints or ball and socket joints.

In one embodiment, the robotic arm is mounted on a turntable on the main tool base for movement about at least the z-axis. In one embodiment, the robotic arm is mounted on a three- or four-axis gimbal to isolate the movements of the main tool base.

In one embodiment, the robotic arm includes a four-axis gimbal so as to isolate movements of the base from those of the end effector. Advantageously, this feature allows the user to hold the main tool base near the eye so as to apply the contact lens to their own eye. This is particularly advantageous because the fear of the approaching lens can cause shaking or other undesirable motion to the main tool base.

In one embodiment, at least one arm of the robotic arm includes a soft and/or resilient material so as to deliver the contact lens in a gentle manner.

In one embodiment, the robotic arms include stepper motors to control their delivery of the contact lens to the target eye.

In one embodiment, the robotic arms include angular stepper motors to control angular articulation of the arms.

In one embodiment, the robotic arms include squiggle motors which include belt drive elements to control the angular articulation of the arms.

In one embodiment, the end effector includes a hinged joint or ball joint to facilitate angular displacement of the contact lens relative to an arm on which it is mounted.

In one embodiment, the end effector is angled so as to facilitate the placement of the contact lens under the upper eyelashes of the target eye.

In one embodiment, the end effector is a vacuum device which grasps the contact lens by vacuum pressure.

In one embodiment, the end effector includes a vacuum fastener.

In one embodiment the end effector includes a clamp for folding the lens into an applicating position.

In one embodiment the end effector clamp jaws are actuated by vacuum pressure.

In one embodiment, the end effector is configured to reverse the vacuum pressure to release and gently propel the contact lens onto the target eye.

In one embodiment, the sensor is a 3D scanner. The 3D scanner may be in one embodiment, a laser scanner, ultrasonic, microwave, or optical scanner. In one embodiment, the 3D scanner is a combination of some or all of those type of scanners, and/or other types of scanners. There may be two cameras placed side by side so as to provide stereoscopic vision for greater depth perception.

In one embodiment, the main tool base includes a steriliser for the end effector. In one embodiment, the steriliser includes a UV light, and/or an autoclave, or chemical bath, or like steriliser.

In one embodiment, the main tool base includes at least one contact lens magazine or reservoir for storing a plurality of contact lenses.

In one embodiment, the main tool base includes a closure for closing the magazine or reservoir. In one embodiment, the processor is configured to cause the opening of the reservoir closure. In one embodiment, the reservoir or magazine closure is a hinged closure, or a sliding closure, or other kind of suitable closure. In one embodiment, the processor is configured to cause the closure of the reservoir or magazine closure.

In one embodiment, the main tool base includes two parallel magazines to store the contact lenses.

In one embodiment, the main tool base includes four magazines to store the contact lenses.

In one embodiment, one or more of the magazines is configured to store individually-wrapped sterile packages which include saline solution to store each contact lens.

In one embodiment, the end effector includes a cutter to cut the sterile packages open to access the contact lens inside. In one embodiment, the cutter is separately provided on the closure or adjacent the closure.

In one embodiment, the magazine includes a biasing element such as a spring to index the contact lenses forward toward the closure to facilitate access by the end effector.

In one embodiment the processor causes the robot arm to reverse the lens application procedure by reaching out to a target eye, grasping the contact lens payload with the end effector, and then withdrawing the contact lens and disposing of it by release into a container.

In accordance with yet another aspect of the present invention there is provided a replaceable storage magazine for contact lenses configured to suit a lens applicator hereindescribed.

Advantageously, embodiments of the apparatus provide a contact lens applicator which compensates for movement relative to a face and target eye in various ways, including via gimbal and other articulating joints, as well as by real-time imaging and scanning of the target face and eye. These features make the apparatus suitable for portable, hand-held self-application of contact lenses, or even by a doctor or any other third person applying it to a patient or other person.

Advantageously, embodiments of the apparatus provide a portable, hand-held extractor for a contact lens from a target eye by real-time assessment of the location of a target face and eye.

Clarifications

In this specification, where a document, act or item of knowledge is referred to or discussed, this reference or discussion is not an admission that the document, act or item of knowledge or any combination thereof was at the priority date:

(a) part of common general knowledge; or
(b) known to be relevant to an attempt to solve any problem with which this specification is concerned.

It is to be noted that, throughout the description and claims of this specification, the word 'comprise' and variations of the word, such as 'comprising' and 'comprises', is not intended to exclude other variants or additional components, integers or steps.

BRIEF DESCRIPTION OF THE DRAWINGS

In order to enable a clearer understanding, a preferred embodiment of the technology will now be further explained and illustrated by reference to the accompanying drawings, in which.

DETAILED DESCRIPTION OF AN EXAMPLE EMBODIMENT

Figure 1:
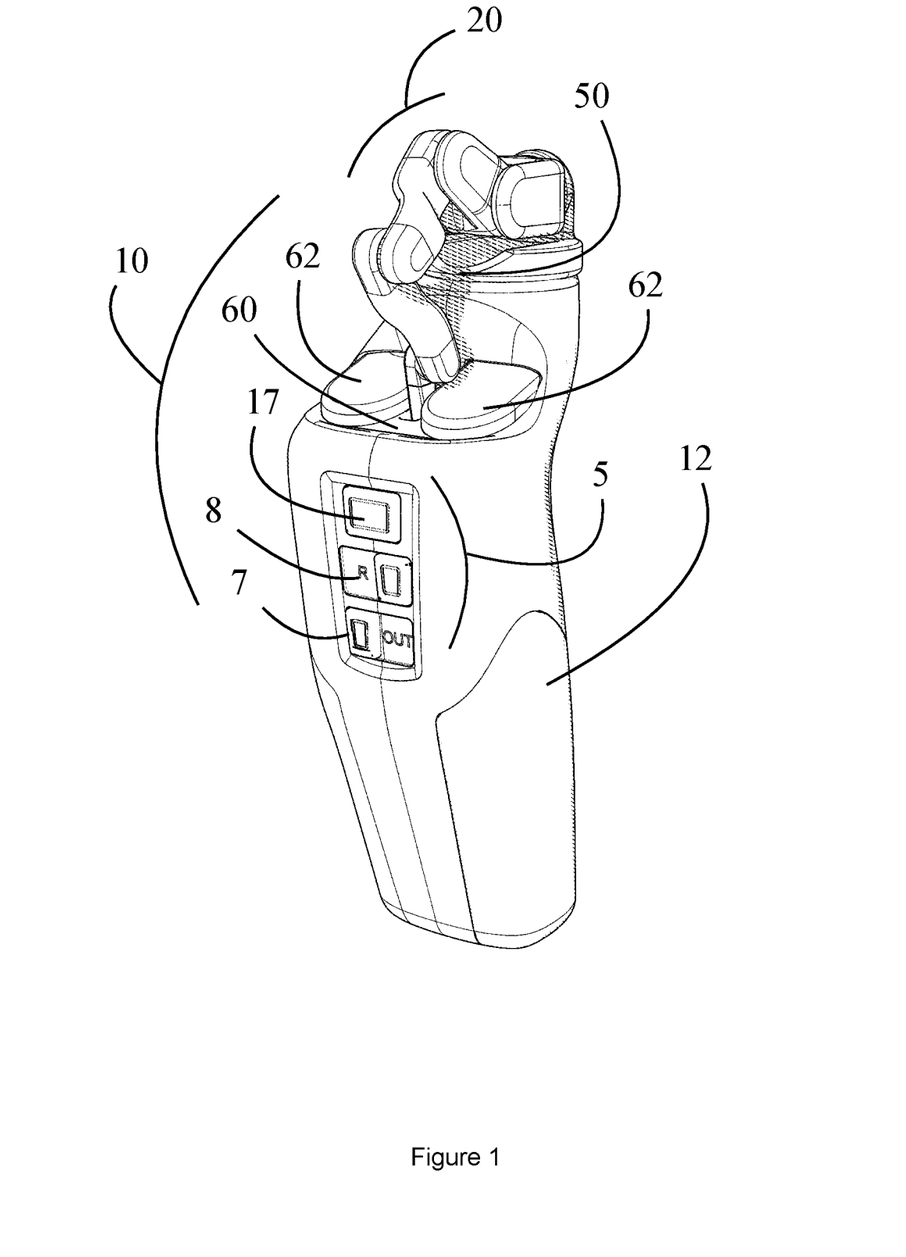
FIG. 1 is a perspective view from in front and right hand side of a contact lens applicator of a preferred embodiment of the present invention, with a robotic arm shown in a stowed position.
Figure 2:
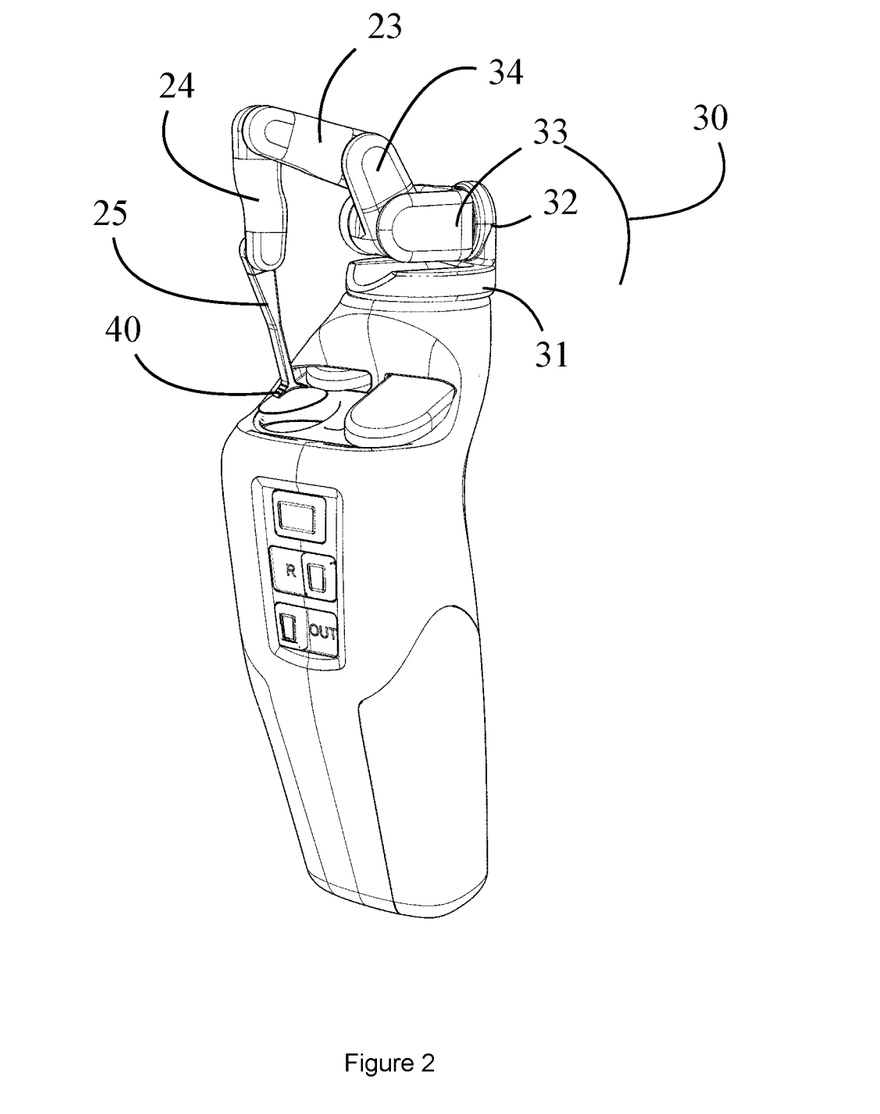
FIG. 2 is a similar view as shown in FIG. 1 but with the robotic arm in a semi-deployed position in which it is loading a contact lens onto the end effector.
Figure 3:
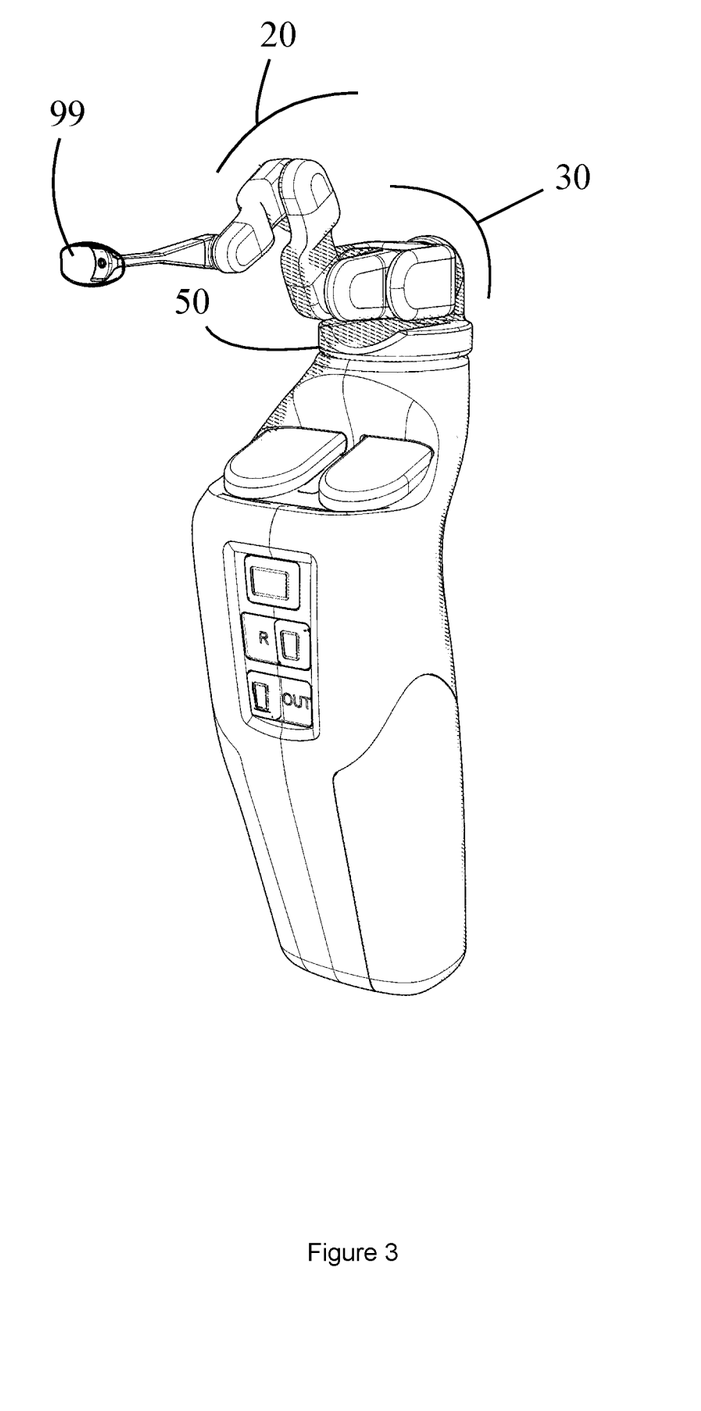
FIG. 3 is a similar view to that shown in FIGS. 1 and 2 with the robotic arm in a deployed position about to deploy a contact lens into an eye (not shown)
Figure 4:
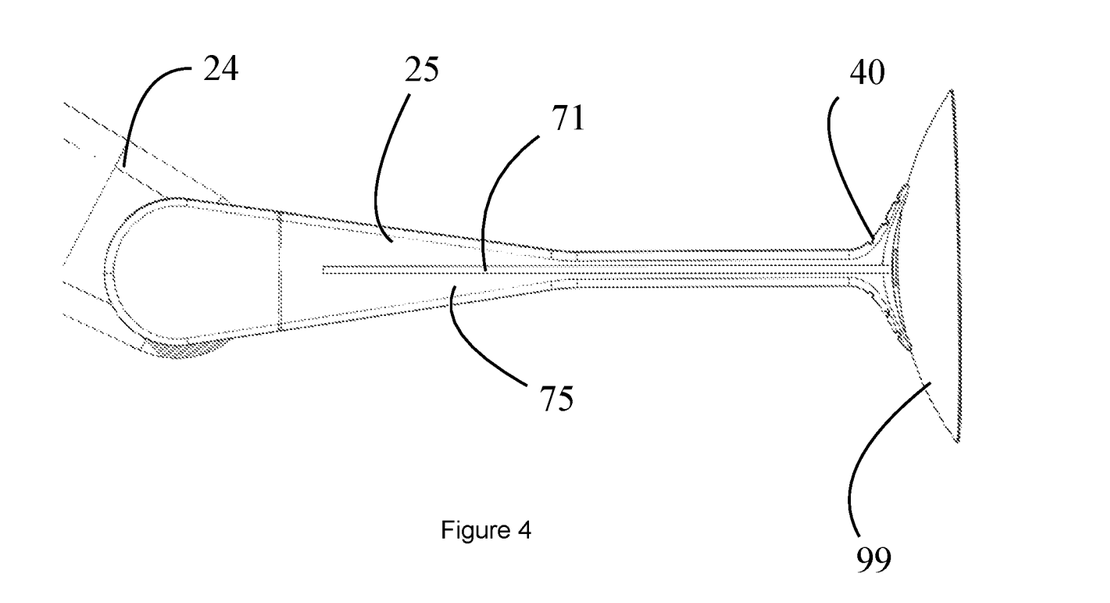
FIG. 4 is a side elevation detail view of the end effector in a deployed position with the contact lens loaded onto the end and in an unfolded position.
Figure 5:
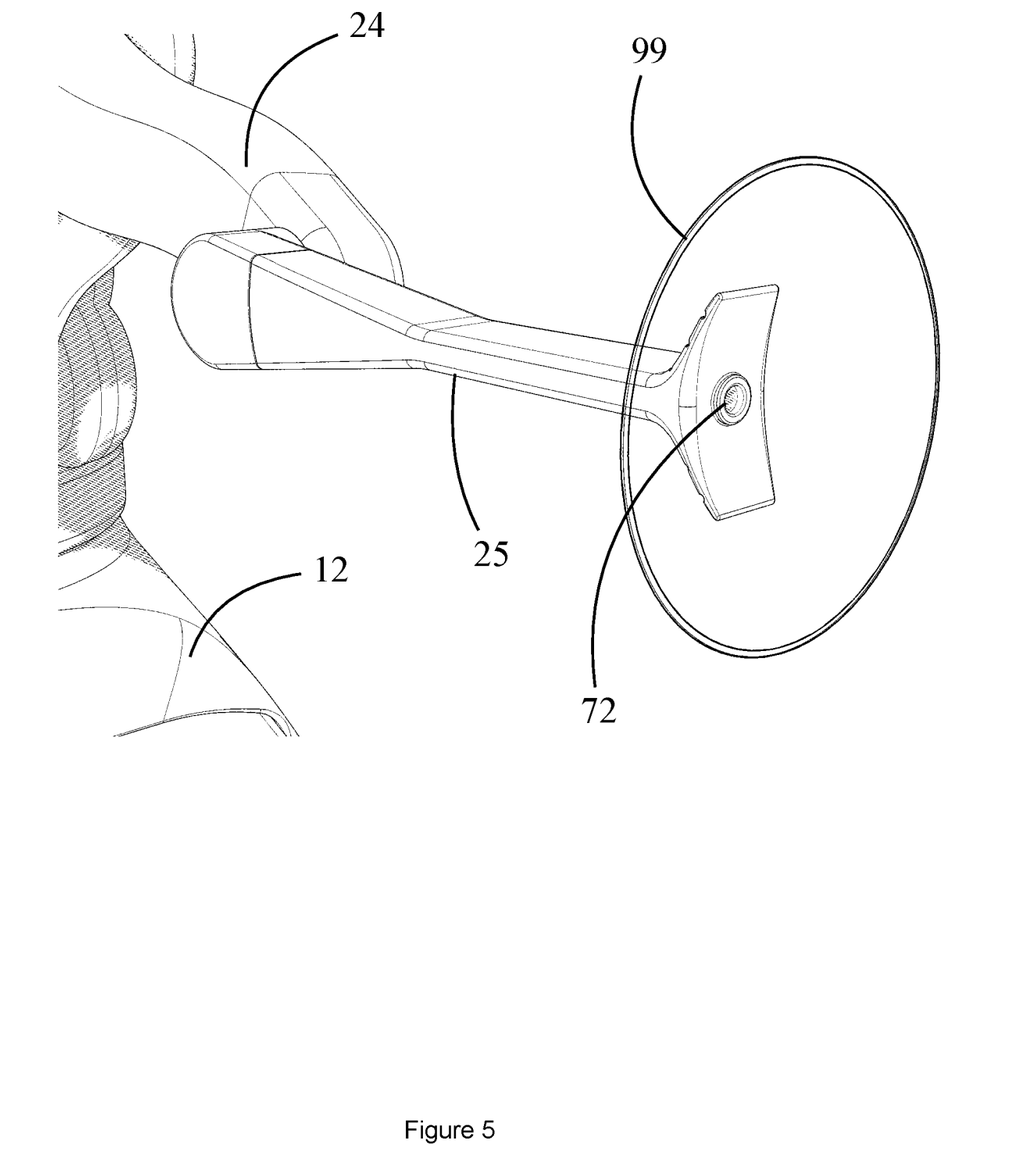
FIG. 5 is a perspective detail view of the robotic arm in a deployed position with the contact lens in an unfolded position, about to fold the lens and deliver a contact lens to a target eye.
Figure 6:
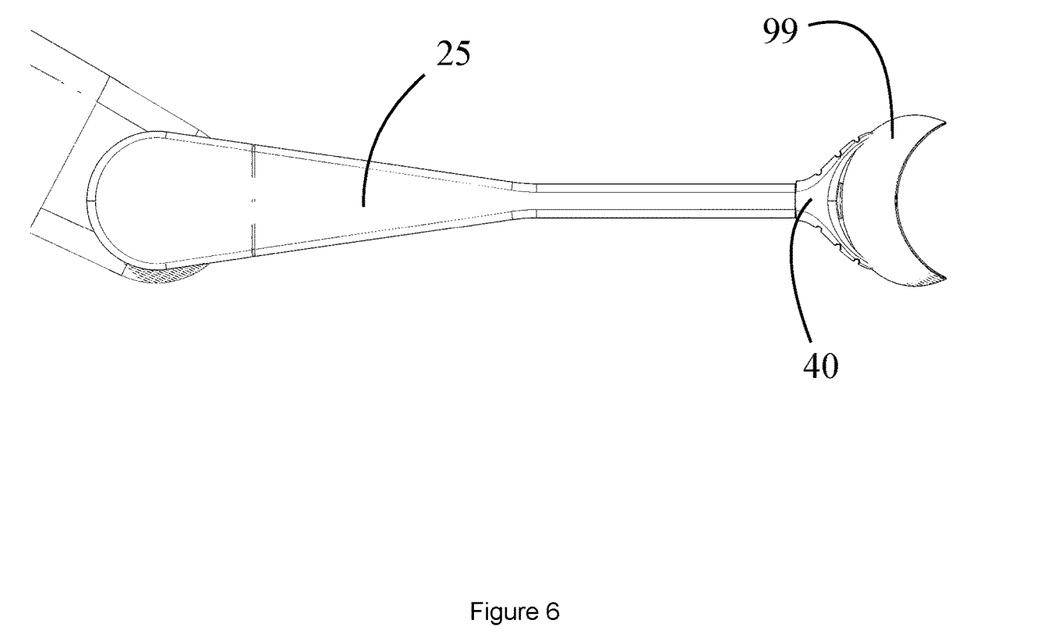
FIG. 6 is a side elevation detail view of the end effector loaded with a contact lens, folded into a folded position for loading into an eye (not shown)
Figure 7:
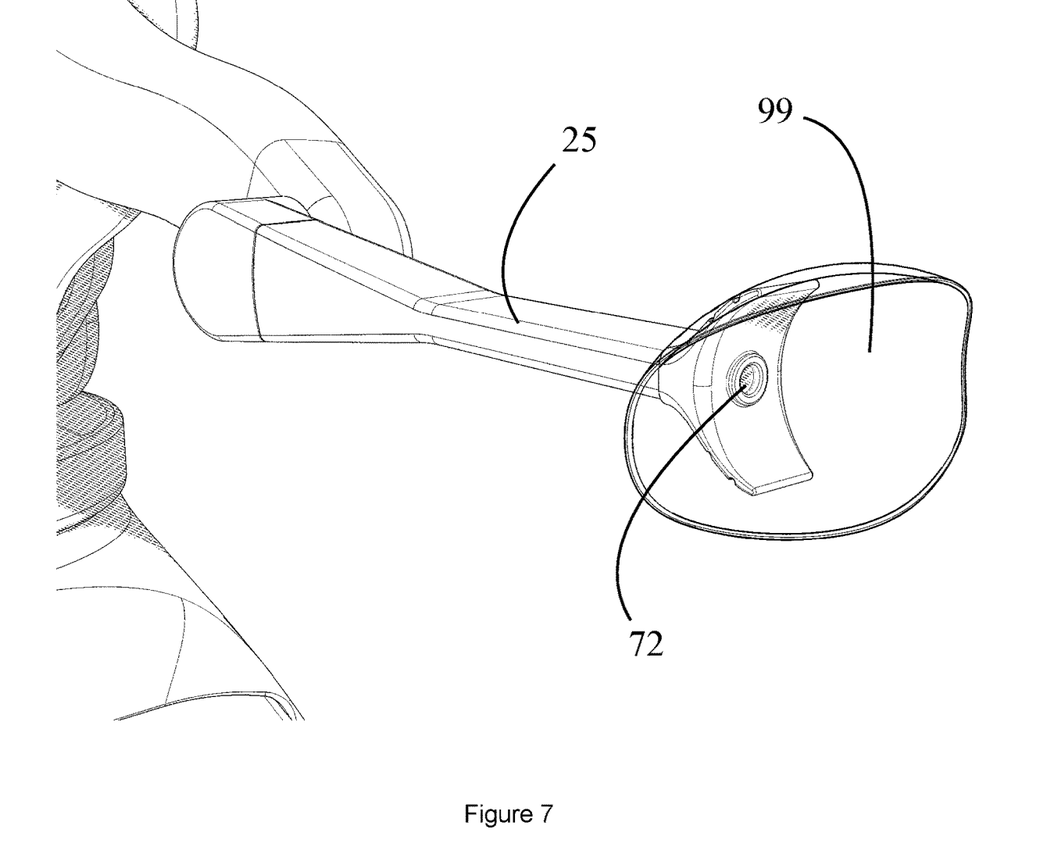
FIG. 7 is a perspective detail view of the end effector loaded as shown in FIG. 6.
Figure 8:
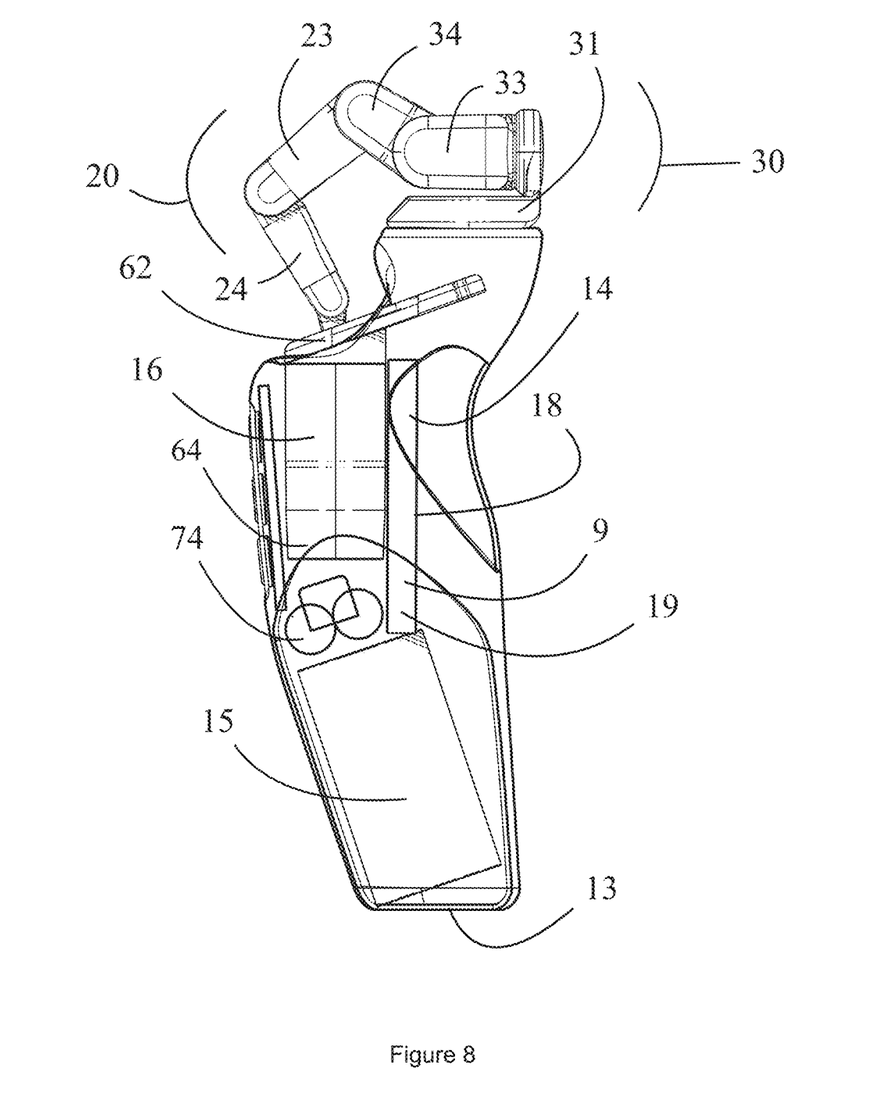
FIG. 8 is a side elevation view of the applicator with the robotic arm in a stowed or cleaning position.
Figure 9:
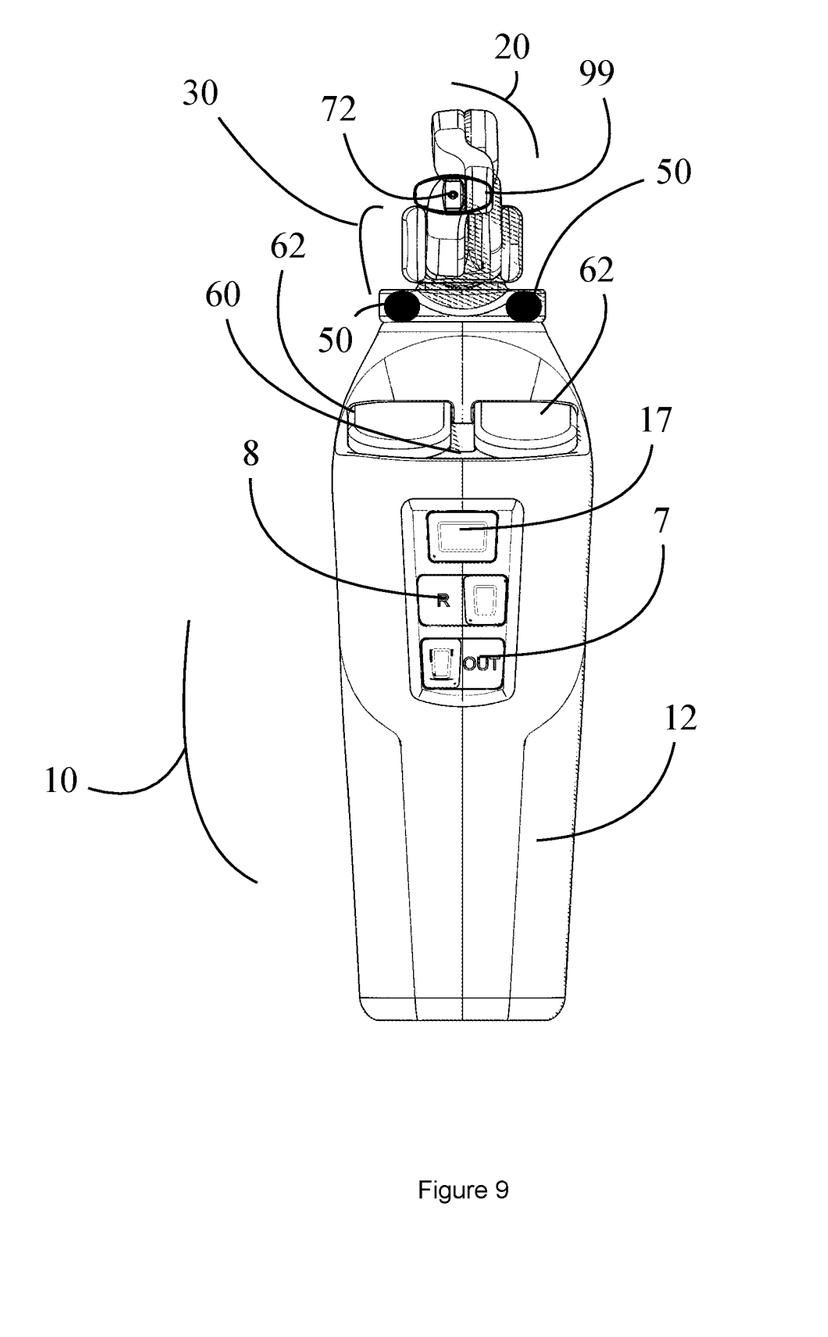
FIG. 9 is a front elevation view of the applicator with the robotic arm in a deployed position.
Figure 10:
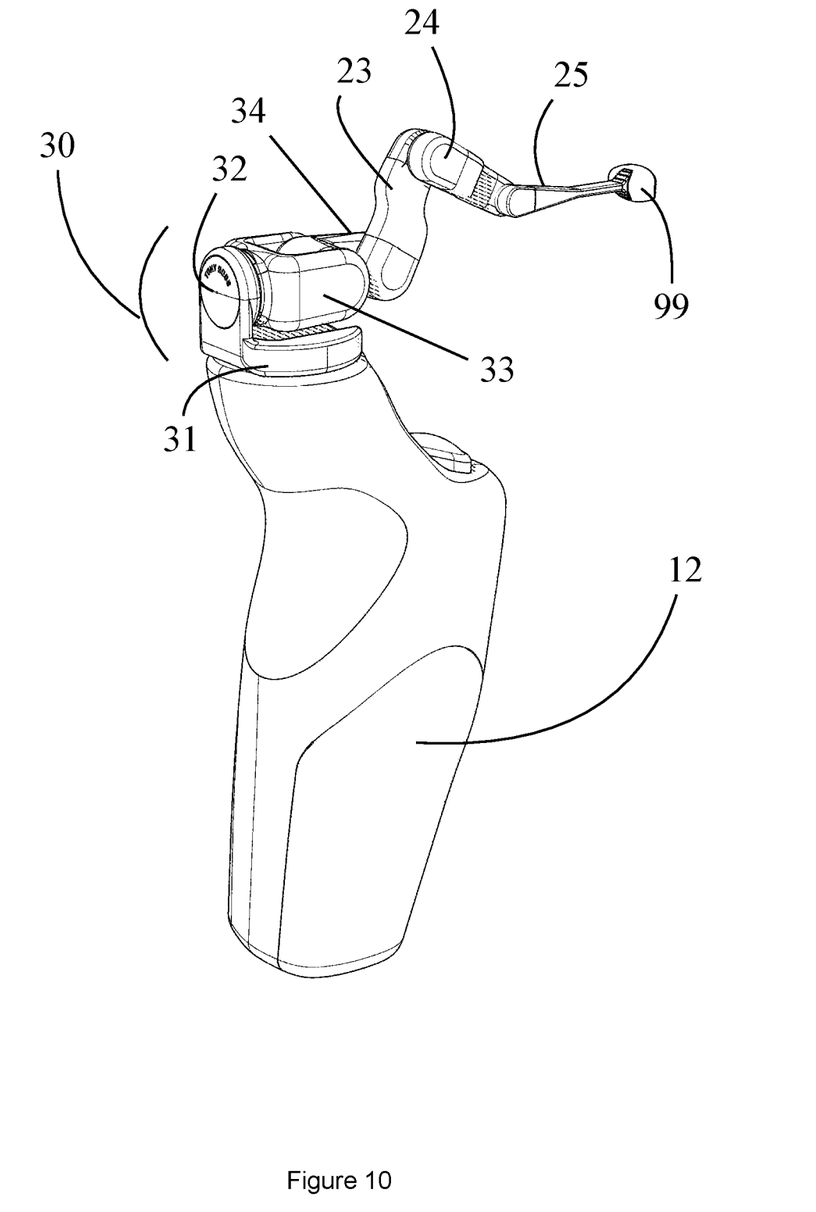
FIG. 10 is an isometric view from behind and the left hand side of the applicator with the robotic arm in the deployed position.

Referring to the drawings there is shown an embodiment of a portable hand-held contact lens applicator tool generally shown at 10, which automatically applies a contact lens 99 to a user's, or a patient's, eye (not shown) with a robotic arm 20.

Advantageously the present technology facilitates portable self-application of a contact lens 99 to a user's own eye.

The contact lens applicator 10 will now be described in detail. It includes a main tool base 12 for housing a control system 14 which includes on board power 15 (in the form of batteries) a processor 18, memory 9, and a networking module 19 for communication with other computing processors via Wi-fi, Bluetooth or other suitable protocol.

The processor 18 includes memory 9, and may be in the form of a Raspberry Pi, PLC, or any other kind of microprocessor which may run any particular kind of operating system suitable for the purpose of operating gimbals 30 and robotic arms with end effectors 40. The Operating system may be AWS, iOS, Linux or the like. The microprocessor may be programmable by a port which can receive code or any other suitable manner. There may be displays that can be connectable to a port for diagnosing errors, or other status indicators.

There is also provided in the main tool base 12 one or more contact lens magazines 16.

The main tool base 12 also includes a charging inlet 13 which is shown on the bottom surface of the tool base.

Also, the main tool base 12 includes user interface 5 which includes program actuator 17, magazine selector 8 and program selector 7. Deployment actuator 17, when actuated, causes the onboard processor 18 to commence the program selected by the program selector 7. The program selector 7 can select between an application routine (applying contact lens to eye) or an extraction routine (removing contact lens from eye).

The lens application routine causes the processor 18 to execute the steps set out below:
grasping a contact lens payload;
identifying target eye for contact lens; and
delivery of contact lens to target eye.

Further programmed steps or routines caused by the processor 18 during another routine or during another routine, on various models of the contact lens applicator tool include:
opening contact lens magazine closure 62;
returning robotic arm 20 to standby position;
detecting obstructions;
retraction of robotic arm 20 if obstruction is encountered;
retraction of robotic arm 20 to standby position when the contact lens is delivered to the target eye.

Another step that the processor 18 can cause to occur is the reversal of vacuum pressure to release and gently propel the contact lens onto the target eye, when the robotic arm is detected to be adjacent the target eye.

The robotic arm 20 is mounted on the tool base 12 and has an end effector 40 mounted on an end of the robotic arm 20 for grasping a contact lens 99 for delivery to an eye of the user.

The robotic arm 20 includes a plurality of articulated arms to facilitate safe delivery of the lens to the eye, the arrangement being such that there is a proximal lens placement arm 23 operatively mounted on the main tool base 12, a second lens placement arm 24 operatively mounted on the proximal lens placement arm 23, and an end effector arm 25 mounted the first intermediate arm 24. The arms 23, 24, and 25 are configured to articulate to make application of the contact lens 99 application to the eye safer than other arrangements. For example, a telescopic arm, if it were to be used, has the potential to misfire and extend uncontrollably into the eye. An articulating arm has a lower likelihood of directly smashing into the eye during deployment.

At the end of the end effector arm 25 is operatively mounted an end effector 40. The end effector is flexible enough to be angled, or the distal arm itself is angled, so that the upper edge of the contact lens 99 hits the eye first, and slides under the upper eyelid of the eye before the distal arm advances and rotates vertically for more secure and easy application. This is part of the application routine which is implemented by the processor 18.

The robotic arm 20 is mounted on a four-axis gimbal 30. The gimbal 30 includes a turntable 31 and three other rotating elements 32, 33 and 34 to isolate the movements of the main tool base 12 from the robotic arm 20. This facilitates portability and self-administering, since it allows the user to hold the main tool base 12 near the eye so as to self-diagnose health issues, and/or self-apply the contact lens to their own eye. This is particularly advantageous in the case of self-application of contact lens because the fear of the approaching lens can cause shaking or other undesirable motion to the main tool base.

The robotic lens placement arms, 23, 24, and 25 include stepper motors to control their delivery of the contact lens 99 to the target eye. The stepper motors may be in the form of squiggle motors 32 which include belt drive elements to control the angular articulation of the arms 23, 24, and 25. The stepper motors relay their positions to the processor 18 so that the processor can understand the location of the end effector 40 relative to the target eye.

The end effector 40 is part of a vacuum apparatus, and in operation it grasps the contact lens 99 by pneumatic force. This is substantially facilitated via a vacuum line which extends through the robotic arm 20, in the form of hollow chambers in the arms, 23, 24 and 25 connected by sealed joints at the ends of the arms 23, 24 and 25.

In order to provide real-time guidance for the robotic arms 20 during the delivery of the contact lens 99 to the eye, the processor 18 in operation receives real time position data on facial features from a 3D scanner 50 which is mounted on the second distal arm 24 in the representations shown, which is a low power laser scanner, ultrasonic, microwave, or optical scanner, stereoscopic camera and any or some or all of those scanner types may be utilised.

The processor 18 also receives data from current or voltage sensors or position sensors such as encoders on the motors in order to provide a degree of obstruction detection or force detection. In operation, if the sensors detect an anomaly, the processor 18 causes the robotic arm 20 to retract into the stowed position, or otherwise stops the advance of the robotic arm 20 towards the eye.

The main tool base 12 further includes a steriliser 60 for the end effector 40. The steriliser includes a UV light which is caused by the processor to switch on when the position sensors inform the processor 18 that the robotic arms are in the stowed position.

The main tool base includes a closure 62 for closing the magazine 16. The processor 18 in operation is configured to cause the opening of the magazine closure 62 at the beginning of the lens deployment sequence. The magazine closure 62 is a sliding closure. After the robotic arm 20 end effector 40 has grasped the contact lens from the magazine 16 of the deployment sequence, the processor 18 causes the closure of the magazine closure 62.

There is provided a fan or an air reservoir 74 in the main tool base 12 for providing vacuum pressure to the end effector 40. The processor during the deployment routine causes the opening of the reservoir or the operation of the fan so as to draw the contact lens against the end effector 40.

The main tool base 12 includes two parallel magazines 16 to store the contact lenses. The magazine includes a biasing element such as a spring 64 to index the contact lenses forward toward the closure 62 to facilitate access by the end effector 40.

The processor 18 in operation (after an extraction routine is actuated) causes the robot arm to reverse the lens application procedure by reaching out to a target eye, grasping the contact lens payload 99 with the end effector 40, and then withdrawing the contact lens and disposing of it by release into a container.

Example Operation: Application

In operation, a user holds the tool body 12 in their hand and uses the interface with their thumb. Picking up the tool body 12 causes the motion sensor to actuate a guiding light from adjacent a camera to indicate to the user where to place their face relative to the robot arm 20. The guide may be in the form of a bar or arm or laser or light which the user can use to place their face in the useful envelope of the tool body 12.

The user selects the magazine 16 (with selector 8) from which they would like to select their lens. Many people have different prescriptions for left and right eyes, so the user selects left or right magazine with selector 8. The light may switch to the other side to indicate to the user to move the tool body relative to the new target eye.

Then the user selects apply or extract (in or out as shown) on the lens program selector 7.

The processor 18 implements a method of delivering a contact lens to a target eye with a robotic arm mounted on a main tool base, the method including the steps of:
- extracting a contact lens 99 from a contact lens reservoir 16 with the robotic arm 20;
- receiving data from an optical scanner 50 regarding a target face;
- delivering the contact lens to a target eye on the target face using real-time data from the optical scanner;
- retracting the robotic arm to a standby position.

The processor 18 first receives a command from the program actuator 17 which releases the end effector 40 from the steriliser 60 and causes the closure 62 to open. Retracting the closure 62 causes a contact lens packet from the magazine to be opened and then a contact lens is exposed for the end effector 40 to grasp.

The processor 18 operates the robotic arm 20 to cause the end effector 40 to reach down, using a stored routine, and grasp the contact lens by vacuum pressure. The processor 18 during the stored routine, monitors the position of each arm in the robotic arm 20 so as to accurately place the end effector 40 into the magazine 16.

To grasp the contact lens 99 and load it onto the end effector 40 the processor 18 activates the vacuum pump (not shown) or opens one or more inlet or outlet valves on the vacuum reservoirs or pneumatic reservoirs 74. The reservoirs 74 and/or vacuum pump are in fluid communication with the central grasping vacuum line 71. The central eye 72 of the end effector 40 is caused by the vacuum pressure in the central grasping vacuum line 71 to grasp a portion of the lens 99 (usually a central portion). The vacuum pressure in the end effector 40, in a separate chamber 75 outside or adjacent the central vacuum line 71, causes the end effector 40 to clamp down on the contact lens 99 and fold it into an applicating position, so it can slip under the eye lid. The end effector 40 is then caused by the processor 18 to move to a ready position in which the sensors 50 are directed at the face of the user.

The robotic arm 20 is caused to move under the guidance of the processor 18 toward the eye of the user. This movement is caused to be done by the processor 18 which processes the image data from the cameras and sensors 50 to advance the end effector 40 towards the eye of the user. There is an option that the image processing be conducted on a nearby computer such as a mobile device connected by wifi or bluetooth protocol, depending on efficiencies and speeds required.

The lens 99 is delivered to the eye and the processor causes the vacuum pump or reservoir 74, in the last one or two mm or so of travel toward the eye, to reverse the vacuum pressure in the line 71, and once contact has been made with the eye and the lens 99 is slipped under the lid, the change in the angle of the end effector 40 is detected by the processor 18. The end effector 40 is then opened by the venting of pressure in the chamber 75 and the lens is gently applied to the eye.

Extraction of the lens 99 from the eye is the reverse process, whereinafter extraction, the lens may be deposited in a discard magazine (not shown) or in a trash receptacle.

The method for extraction includes a contact lens presence check step. The contact lens presence check is conducted with camera 50 for watermark on contact lens; if watermark is detected, then proceed with extraction routine. The camera 50 sends data to processor 18 for onboard processing or off-site processing via network card. The contact lens watermark is applied at manufacture.

The extraction routine includes the step of checking for presence of eye in operation envelope, with camera 50.

The extraction routine includes the step of providing guidance to the user as to placement of the eye in the operation zone. This is done in the embodiment shown by actuation of a blue light which becomes visible when the user is in front of, and close enough to, the operation zone. Two lights are provided in order to provide guidance to the eyes and they are both visible to the user when the user's eyes are in the right location for application or extraction of one or more lenses. The lights may be LEDs or other kinds of lights or lamps—incandescent, or other light. The guides may be apertures in the tool body 12 such that they can be seen through when the eye is in the right place. The apertures may be adjustable. The lights may be adjustable.

The extraction routine commences when the actuator 17 is depressed and the eye is in the operation zone. During the extraction routine, the gimbal 30 motors operate to compensate for user movements of the body 12, and then the lens placement arms 23, 24, 25 operate to extend and the end effector 40 fastens the lens 99 when it approaches, since the vacuum tube 72 is actuated.

Advantageously, the method includes the step of compensating for movements of a base on which the robotic arm is mounted, to facilitate self-administration of the contact lens while holding the contact lens in a user's own hand.

Advantages

Advantageously, embodiments of the apparatus provide a contact lens applicator which compensates for movement relative to a face and target eye in various ways, including via gimbal and other articulating joints, as well as by real-time imaging and scanning of the target face and eye. These features make the apparatus suitable for portable, hand-held self-application of contact lenses, or even by a doctor or any other third person applying it to a patient or other person.

Advantageously, embodiments of the apparatus provide a portable, hand-held extractor for a contact lens from a target eye by real-time assessment of the location of a target face and eye.

Clarifications

Modifications and improvements to the invention will be readily apparent to those skilled in the art. Such modifications and improvements are intended to be within the scope of this invention.

What is claimed is:

1. A contact lens applicator which automatically applies and/or removes a contact lens to a user's, or a patient's, eye, the contact lens applicator including:
    a main tool base for housing a control system;
    a robotic arm including a plurality of articulated arms connected together by hinged joints or ball and socket joints, the robotic arm mounted on the tool base and in communication with the control system;
    an end effector mounted on an end of the robotic arm for grasping a contact lens for delivery to an eye of the user.

2. The contact lens applicator in accordance with claim 1 wherein the robotic arm is mounted on a turntable on the main tool base for movement about at least the z-axis.

3. The contact lens applicator in accordance with claim 1 wherein the robotic arm is mounted on a three- or four-axis stabiliser to isolate the movements of the main tool base.

4. The contact lens applicator in accordance with claim 1 wherein at least one of the plurality of arms of the robotic arm includes a soft and/or resilient material so as to deliver the contact lens in a gentle manner.

5. The contact lens applicator in accordance with claim 1 wherein the articulated arms include stepper motors or squiggle motors which include belt drive elements to control the delivery of the contact lens to the target eye by the robotic arm.

6. The contact lens applicator in accordance with claim 1 wherein the end effector includes a hinged joint or ball joint to facilitate angular displacement of the contact lens relative to an arm on which it is mounted.

7. The contact lens applicator in accordance with claim 1 wherein the end effector is a vacuum device which grasps the contact lens by vacuum pressure.

8. The contact lens applicator in accordance with claim 1 wherein the end effector includes a clamp including a pair of clamp jaws for folding the lens into an applicating position.

9. The contact lens applicator in accordance with claim 8 wherein the end effector clamp jaws are actuated by vacuum pressure.

10. The contact lens applicator in accordance with claim 1 wherein a sensor in the form of a 3D scanner selected from the group consisting of: a laser scanner, ultrasonic, microwave, or optical scanner, is provided to control the movement of the robotic arm and end effector.

11. The contact lens applicator in accordance with claim 1 further including a steriliser selected from the group consisting of: a UV light; an autoclave; and a chemical bath configured to sterilise the end effector.

12. The contact lens applicator in accordance with claim 1 wherein the main tool base includes one, two three or four contact lens magazines or reservoirs for storing and dispensing a plurality of contact lenses.

13. The contact lens applicator in accordance with claim 12 wherein the main tool base includes a closure for closing one or more of (i) the contact lens, (ii) the magazines, and (iii) the reservoirs, the closure being a sliding or a hinged closure.

14. The contact lens applicator in accordance with claim 13 wherein the one or more contact lens magazines or reservoirs include a spring to index the contact lenses in the contact lens magazines or reservoirs forward toward the closure to facilitate access by the end effector.

15. The contact lens applicator in accordance with claim 12 wherein the robotic arm is caused and/or configured by the control system to execute a programmed sequence of tasks including:
    grasping a contact lens;
    identifying target eye for placement of the contact lens thereon;
    delivery of the contact lens to the target eye;
    cleaning end effector;
    opening or closing one or more contact lens magazine closures;
    detecting obstructions;
    retraction of robotic arm if obstruction is encountered; and
    retraction of robotic arm to standby position when the contact lens is delivered to the target eye.

16. The contact lens applicator in accordance with claim 15 wherein the control system causes the robot arm to
    extend a robot arm having an end effector to a target eye having a contact lens mounted thereon,
    grasp the contact lens with the end effector, and then withdraw the contact lens from the eye and
    release the contact lens into a container.

17. The contact lens applicator in accordance with claim 1 wherein one or more magazines is configured to store individually-wrapped sterile packages which include saline solution to store each contact lens.

18. The contact lens applicator in accordance with claim 1 wherein there is provided a guide selected from the group consisting of: a light; a laser; a bar configured to guide the user as to where they should place their eye relative to the robot arms and main tool base.

19. A method of delivering a contact lens to a target eye with a robotic arm mounted on a main tool base, the method including the steps of:

extracting a contact lens from a contact lens magazine with the robotic arm;
receiving in a computer processor, data from one or more sensors regarding a target eye;
delivering by manipulation of a robotic arm and an end effector the contact lens to a target eye using real-time data from the sensor;
retracting the robotic arm to a stowed position;
compensating for movements of a base on which the robotic arm is mounted, to facilitate self-administration of the contact lens while holding the main tool base in a user's own hand.

\* \* \* \* \*